Figure 1:
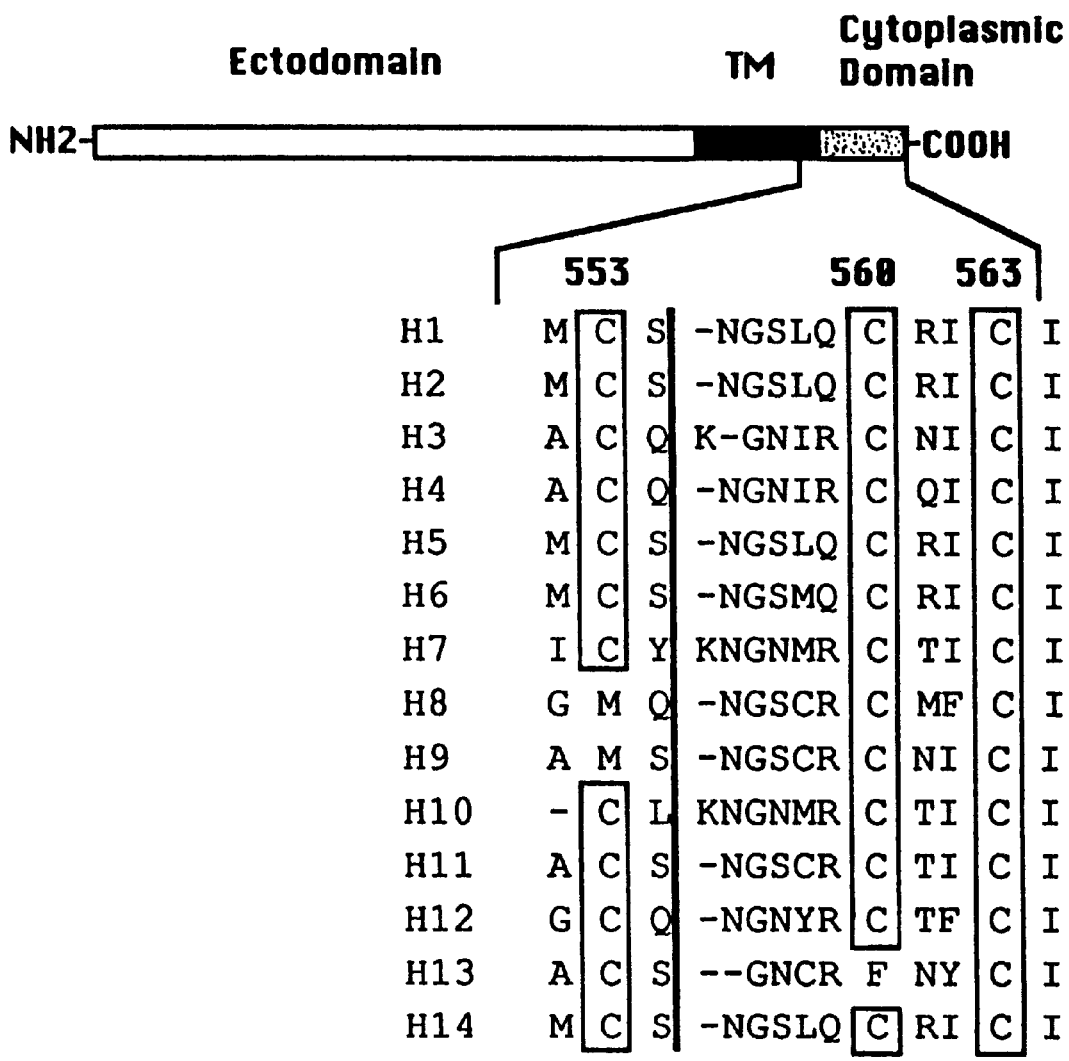

US006150131A

United States Patent [19]
Palese

[11] Patent Number: 6,150,131
[45] Date of Patent: *Nov. 21, 2000

[54] METHOD FOR DETECTING ANTIVIRALS THAT INHIBIT ACYLATION/ PALMITYLATION OF HEMAGGLUTININ

[76] Inventor: Peter Palese, 414 Highwood Ave., Leonia, N.J. 07605

[*] Notice: This patent issued on a continued prosecution application filed under 37 CFR 1.53(d), and is subject to the twenty year patent term provisions of 35 U.S.C. 154(a)(2).

[21] Appl. No.: 08/737,841

[22] PCT Filed: May 17, 1995

[86] PCT No.: PCT/US95/06292

§ 371 Date: Mar. 6, 1997

§ 102(e) Date: Mar. 6, 1997

[87] PCT Pub. No.: WO95/32309

PCT Pub. Date: Nov. 30, 1995

Related U.S. Application Data

[63] Continuation-in-part of application No. 08/246,643, May 20, 1994, abandoned.

[51] Int. Cl.[7] ............................. C12P 21/06; G01N 33/53
[52] U.S. Cl. ........................ 435/69.1; 435/7.1; 435/7.72
[58] Field of Search ..................... 435/69.1, 7.1, 435/7.72

[56] References Cited

U.S. PATENT DOCUMENTS

| | | | |
|---|---|---|---|
| 5,077,210 | 12/1991 | Eigler et al. | 435/176 |
| 5,166,057 | 11/1992 | Palese et al. | |
| 5,169,756 | 12/1992 | Ranby et al. | 435/7.4 |

OTHER PUBLICATIONS

Journal of Virology, Mar. 1996, p. 1406–1414, "Palmitylation of the Influenza Virus Hemagglutinin (H3) Is Not Essential for Virus Assembly or Infectivity", by H. Jin et al.

Naim et al., 1992, "Effects of altering palmitylation sites on biosynthesis and function of the influenza virus hemagglutinin", J Virol 66(12):7585–7588.

Simpson and Lamb, 1992, "Alterations to influenza virus hemagglutinin cytoplasmic tail modulate virus infectivity", J Virol 66(2):790–803.

Naeve and Williams, 1990, "Fatty acids on the A/Japan/305/ 57 influenza virus hemagglutinin have a role in membrane fusion", EMBO J 9(12):3857–3866.

McIlhinney, 1990, "The fats of life: The importance and function of protein acylation", TIBS 15:387–391.

Schlesinger and Malfer, 1982, "Cerulenin blocks fatty acid acylation of glycoproteins and inhibits vesicular stomatitis and Sindbis virus particle formation", J Biol Chem 257(17):9887–9890.

Naim, et al, "Effects of altering palmitylation sites . . . " J. Virol. 66(12):7585–7588, 1992.

Naeve, et al, "Fatty Acids on the A/Japan/305/ 57 influenza . . . " EMBO J. 9(12):3857–3866, 1990.

Simpson, et al, "Alterations to influenza virus hemagglutinin . . . " J. Virol. 66(2):790–803, 1992.

Schlesinger, et al, "Coerulenin blocks fatty acid acylation . . . " J. Biol. Chem. 257(17):9887–90, 1982.

McIlhinney, 1990, "The Fats of Life . . ." TIBS 15:387–391, 1990.

*Primary Examiner*—Jeffrey Stucker
*Assistant Examiner*—Brett Nelson

[57] ABSTRACT

The present invention relates to assays for the identification of compounds that block palmitylation of influenza virus HA and inhibit virus assembly. In another aspect of the invention, the compounds which inhibit virus assembly, infection and/or replication and which demonstrate a good therapeutic index may be used to treat influenza infection.

9 Claims, 5 Drawing Sheets

METHOD FOR DETECTING ANTIVIRALS THAT INHIBIT ACYLATION/PALMITYLATION OF HEMAGGLUTININ

This application is the national phase of PCT/US95/06292 filed May 17, 1995 and a Continuation-in-Part of application Ser. No. 08/246,643, filed May 20, 1994, abandoned, which is incorporated herein by reference in its entirety.

1. INTRODUCTION

The present invention relates to assays for the identification of compounds that block palmitylation of influenza virus hemagglutinin (HA), and inhibit infectious virus formation. The invention also relates to the use of such compounds as antiviral agents for the treatment of flu.

2. BACKGROUND OF THE INVENTION

The hemagglutinin (HA) of influenza virus is the major surface antigen and is one of the best characterized membrane glycoproteins. It has receptor-binding and fusion activity, which are both necessary for the initiation of viral infection. The protein contains a large ectodomain that carries receptor and fusion activities, a stretch of hydrophobic amino acids which constitutes the transmembrane domain, and a short cytoplasmic tail. This cytoplasmic tail contains 10–11 amino acids, depending on the subtype of the HA (Ward, 1981, Curr. Top. Microbiol. Immunol. 94/95:1–74; FIG. 1). Comparison of the HA sequences in this region reveals that 5 amino acids are highly conserved and that they are identical in 11 of the 14 known subtypes (Doyle et al., 1985, J. Cell Biol. 100:704–714; Kawaoka et al., 1990, Virology 179:759–767; Nobusawa et al., 1991, Virology 182:475–485; Simpson & Lamb, 1992, J. Virol. 66:790–803). Two of these conserved residues are cysteines (positions 560 and 563) and a third highly conserved cysteine is located in the membrane-anchoring domain (position 553) (FIG. 1). It as previously been shown that the conserved cysteines of subtype H2, H3 and H7 HAs are post-translationally modified by covalent addition of palmitic acids (Naeve & Williams, 1990, EMBO J. 9:3857–3866; Naim et al., 1992, J. Virol. 66:7585–7588; Schmidt & Lambrecht, 1985, J. Gen. Virol. 66:2635–2647; Steinhauer et al., 1991, Virology 184:445–448). The levels of palmitylation have been quantified for the A/Japan/305/57 HA (H2), whose 17 carboxy-terminal amino acids are identical to those of the A/WSN/33 HA (H1). The cysteines at positions 560 and 563 (FIG. 1) appear to be highly modified, with position 563 incorporating at least half of the fatty acid label, whereas position 553 incorporates only about 10% of the total palmitate (Naim et al., 1992, J. Virol. 66:7585–7588).

The extent and significance of palmitylation of viral proteins is not yet fully understood (reviewed in McIlhinney, 1990, TIBS 15:387–391). The fact that HeLa cells are refractory to influenza virus growth has been ascribed to a defect in palmitylation of this cell line, but other mechanisms responsible for the abortive infection in HeLa cells cannot be ruled out (Portincasa et al., 1992, Res. Virol. 143:401–406). Experiments using hydroxylamine to remove lipid from viral proteins have suggested that the fatty acid moiety is important for membrane fusion (Schmidt & Lambrecht, 1985, J. Gen. Virol. 66:2635–2647). Another report used the antibiotic cerulenin to inhibit acylation and has implicated the lipid in viral release (Schlesinger & Malfer, 1982, J. Biol. Chem. 257:9887–9890). However, these interpretations are not definitive since hydroxylamine might affect the protein structure and cerulenin is known to exert a general toxic effect. For vesicular stomatitis virus (VSV) it has been reported that the elimination of the palmitylation site in the G protein has no effect on membrane fusion or glycoprotein incorporation into virions (Whitt et al., 1989, J. Virol. 63:3569–3578). Studies with alphaviruses have shown that the elimination of either one of the two palmitylation sites in the carboxy terminus of the glycoprotein E2 decreases the efficiency of virus budding (Ivanova & Schlesinger, 1993, J. Virol. 67:2546–2551), and that a mutant with changes in both palmitate addition sites was not viable (Gaedigk-Nitschko & Schlesinger, 1991, Virology 183:206–214).

There is one report which suggests that the A/Japan/305/57 HA (H2) requires palmitate for membrane fusion (Naeve & Williams, 1990, EMBO J. 9:3857–3866). However, this finding has not been supported by other workers using either H2, H3 or H7 subtype HAs (Naim et al., 1992, J. Virol. 66:7585–7588; Simpson & Lamb, 1992, J. Virol. 66:790–803; Steinhauer et al., 1991, Virology 184:445–448; Veit et al., 1991, J. Virol. 65:2491–2500). It has been shown that substitution of the conserved cysteines at positions 553, 560 or 563 by serine (H2 and H3) or alanine (H7) did not significantly affect HA biosynthesis, intracellular transport or receptor-binding activity, when expressed from recombinant plasmid DNA or SV40 vectors (Doyle et al., 1985, J. Cell Biol. 100:704–714; Lazarovits & Roth, 1988, Cell 53:743–752; Naeve & Williams, 1990, EMBO J. 9:3857–3866; Naim et al., 1992, J. Virol. 66:7585–7588; Simpson & Lamb, 1992, J. Virol. 66:790–803; Steinhauer et al., 1991, Virology 184:445–448; Veit et al., 1991, J. Virol. 65:2491–2500). In fact, HA proteins with mutations in two (Simpson & Lamb, 1992, J. Virol. 66:790–803) or all three (Naim et al., 1992, J. Virol. 66:7585–7588) palmitate addition sites complemented an influenza virus with a temperature-sensitive mutation in the HA.

Recently, Naim and Roth (Naim & Roth, 1993, J. Virol. 67:4831–4841) have extended their studies of the role of the cytoplasmic tail by expressing HA variants from recombinant SV40 viruses in influenza virus-infected cells. Although chimeric HAs with foreign cytoplasmic sequences were efficiently excluded from viral envelopes, HAs which lacked a cytoplasmic tail were incorporated into virions. Similarly, Simpson and Lamb (Simpson & Lamb, 1992, J. Virol. 66:790–803) showed that HA mutants lacking a cytoplasmic tail were incorporated into viral particles, but the particles were found to be non-infectious. This would indicate that the conserved cytoplasmic sequences are not required for the incorporation of HA into virions but that the cytoplasmic tails of the HAs are necessary for the infectivity of the virus. However, data presented here using a different assay system indicate a role for these cysteine residues in the formation of infectious influenza virus.

3. SUMMARY OF THE INVENTION

The present invention relates to assays for the identification of compounds that block palmitylation of influenza virus HA and inhibit virus assembly. In another aspect of the invention, the compounds which inhibit virus assembly, infection and/or replication and which demonstrate a good therapeutic index may be used to treat influenza infection.

The invention is based, in part, on the Applicant's discovery that mutations of palmitylation sites of influenza virus HA affect virus formation, and that inhibition of palmitylation of HA inhibits virus replication possibly by interfering with viral assembly. Using reverse genetics techniques, transfectant influenza viruses were constructed which have changes in their HA genes. The advantage of the reverse genetics procedure is that the effects of mutations can be analyzed in the context of infectious virus. Transfectant influenza viruses containing mutations at the conserved palmitate addition sites of the HA were isolated in order to study the effects of the changes on the phenotype of the viruses. The data presented indicate a role for the cysteine residues in the formation of infectious influenza virus. Moreover, it was found that one of the palmitate addition sites, the cysteine at position 563 of the cytoplasmic tail is required for infectious particle formation. While not limited to any explanation or theory of operation, it is proposed that palmitylation of the conserved carboxy terminus of influenza HA is required for proper anchoring of the viral protein and for post-translational trafficking of the HA protein required for viral assembly.

In one embodiment, the assays of the present invention are designed to target a step subsequent to the synthesis of palmitate. Such assays allow for the identification of compounds that interfere with palmitylation of viral gene products and inhibit infectious virus formation, yet do not interfere with the synthesis of palmitate, a key fatty acid important for cell metabolism and energy production. Therefore, inhibitory compounds that do not disrupt important cellular pathways for energy generation may be identified using these assays of the present invention.

In another aspect of the invention, assays are designed to detect compounds that interfere with or inhibit the biosynthesis of palmitate such that an antiviral effect is achieved. For example, infectious virus formation may be depressed at reduced levels of palmitate that are not toxic to the cell; reduced levels of palmitate may be selectively toxic for virus-infected cells; or a combination of the two may achieve the desired antiviral effect.

4. DESCRIPTION OF THE DRAWINGS

FIG. 1. Comparison of the carboxy terminal amino acid sequences of the HAs of 14 different influenza A virus subtypes (SEQ ID NOS: 1–4) (Doyle et al., 1985, J. Cell Biol. 100:704–714; Kawaoka et al., 1990, Virology 179:759–767; Nobusawa et al., 1991, Virology 182:475–485; Simpson & Lamb, 1992, J. Virol. 66:790–803). Cysteine residues are boxed and vertical bar indicates the division between the transmembrane (TM) and the cytoplasmic tail (reviewed in Ward, 1981, Curr. Top. Microbiol. Immunol. 94/95:1–74). The numbering of the conserved cysteines refers to the H1 subtype HA (Hiti et al., 1981, Virology 111:113–124).

Figure 2:
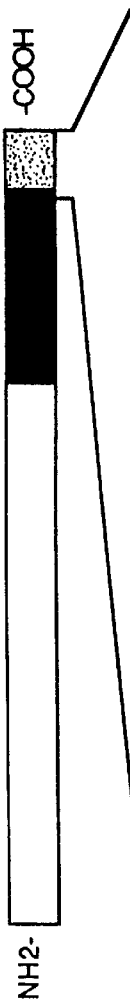
Figure 3A:
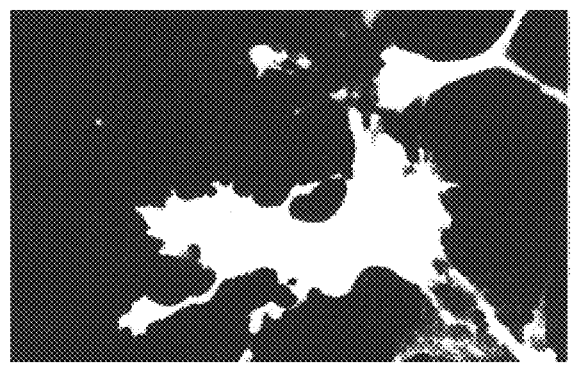
Figure 3B:
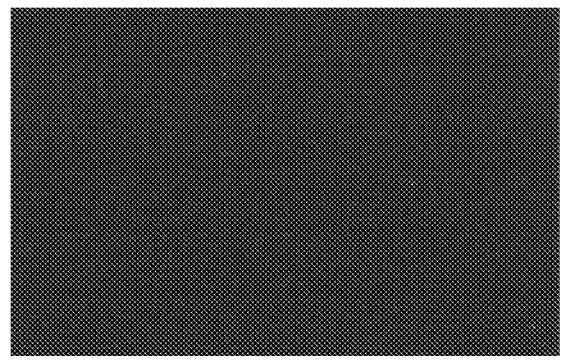
Figure 3C:
Figure 3D:
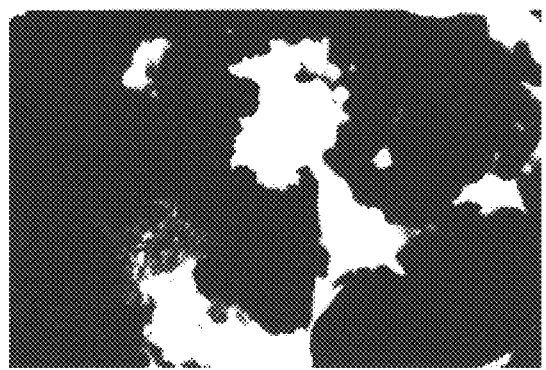
Figure 3E:
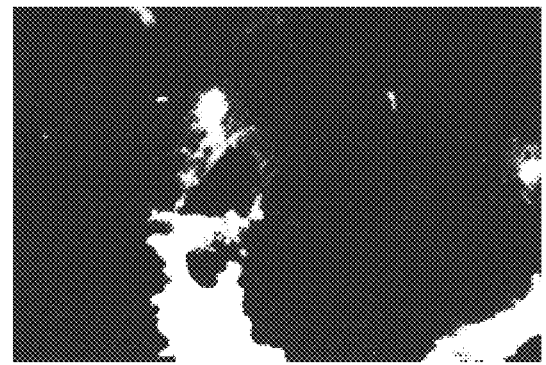
Figure 3F:
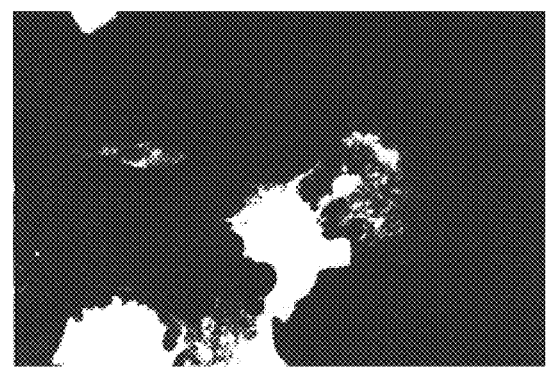

FIG. 2. Amino acid sequence of the carboxy terminus of wild-type influenza A/WSN/33 (SEQ ID NOS: 15–16) and mutant HA proteins. Left column lists the names of the plasmids used. For example, construct pC553S has the cysteine in position 553 exchanged by serine. In the right column rescued mutants are indicated by (+). TM, transmembrane region; Cyto, cytoplasmic tail; wild-type: plasmid pT3WSN-HA/HindIII.

FIGS. 3A–3F. Surface expression of wild-type and mutant HA proteins in transiently transfected, vaccinia infected (vTF7.3) COS-7 cells. Transfected plasmids: (A) pSVK3/HA(wild-type), (B) mock transfected, (C) PSVK3/C560A/C563A, (D)/PSVK3/C563A, (E)PSVK3/C560S, (F)PSVK3/C553S/C560S/C563S.

Figure 4A:
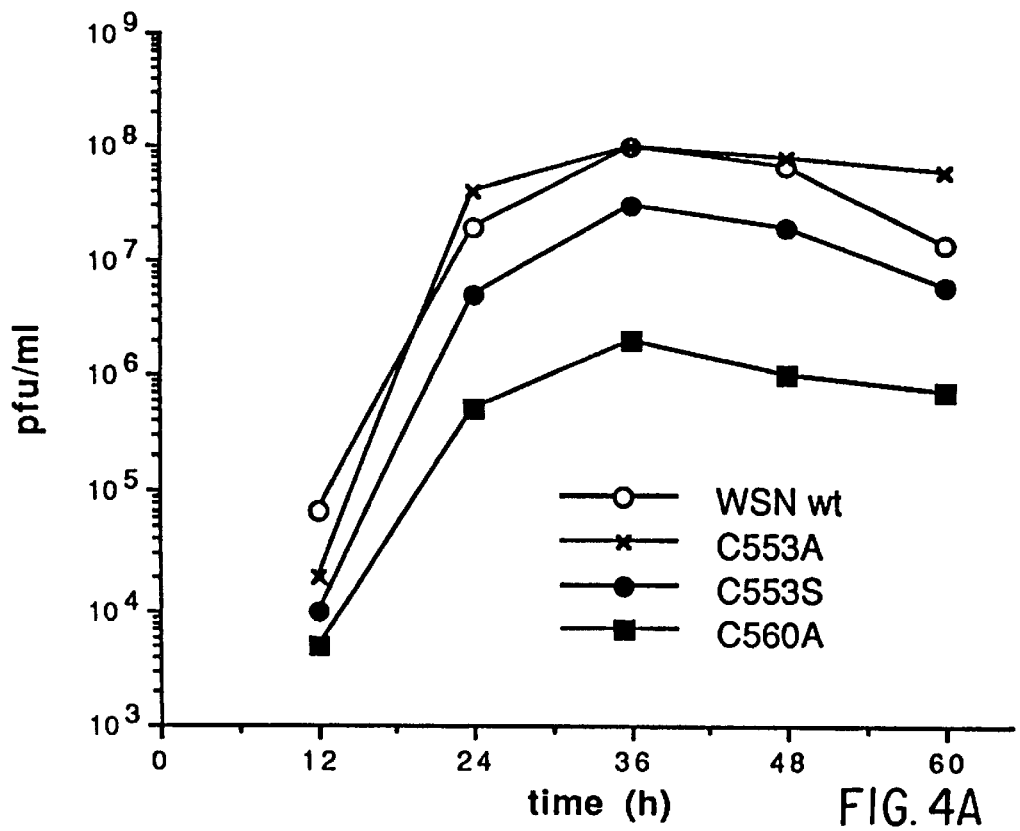
Figure 4B:
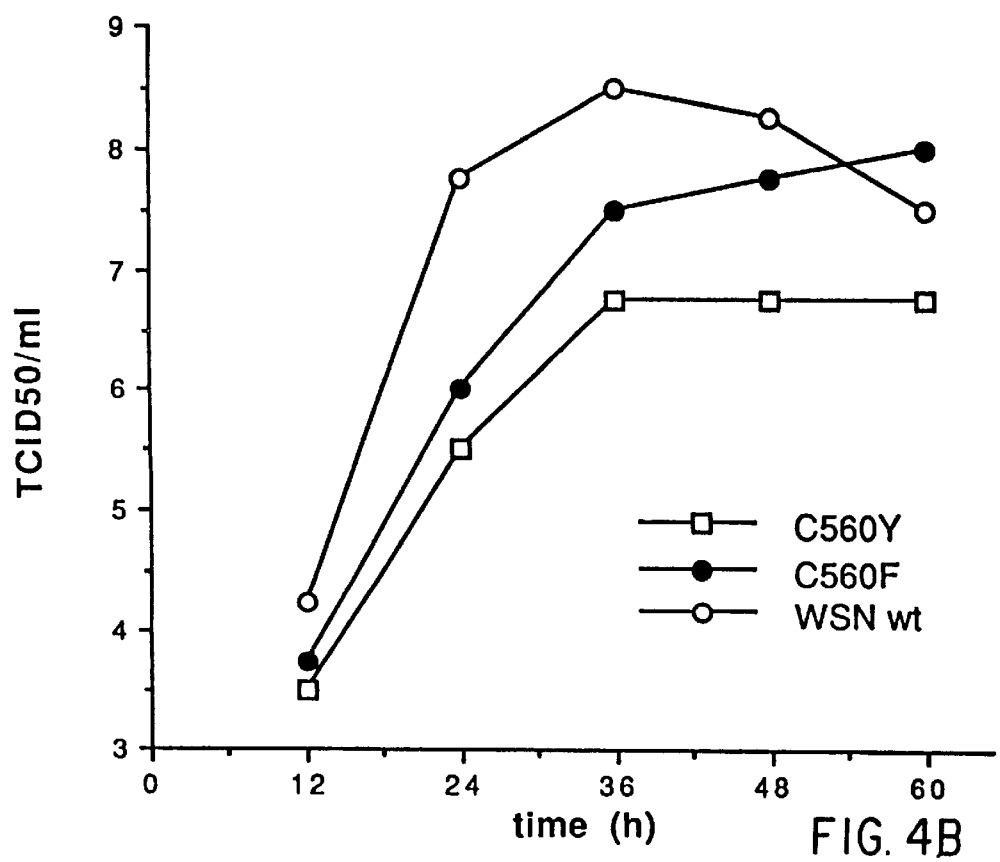

FIGS. 4A–4B. Growth characteristics of wild-type and transfectant viruses on MDBK cells determined by plaque titration (A) and $TCID_{50}$-assay on MDBK cells (B). It should be noted that mutant C560Y does not form discreet plaques and thus the $TCID_{50}$ assay was used for titration of virus yields.

5. DESCRIPTION OF THE INVENTION

The present invention relates to the identification and use of compounds that interfere with or inhibit the palmitylation of viral proteins required for viral infectivity, replication and/or assembly. Assays are described to identify compounds that inhibit the covalent attachment of palmitate to the viral protein, remove the attached palmitate from the viral protein, or inhibit the biosynthesis of palmitate and disrupt the formation of infectious virus. Inhibitory compounds which are relatively non-toxic, e.g., display a good therapeutic index, may be utilized as antiviral agents for the treatment of viral infection in animals, including humans.

For clarity of discussion, the invention is described in the subsections below for influenza virus HA. However, the principles may be analogously applied to other viruses in which palmitylation of viral proteins plays a key role in viral replication and assembly. Indeed, glycoproteins present in a number of enveloped viruses have been shown to contain palmitic acid residues (Schmidt, 1982, Virology 116:327–338; Schmidt et al., 1979, Cell 17:813–819; Schmidt & Schlessinger, 1979, Proc. Natl. Acad. Sci. (Wash) 76:1687–1691; Klochmann & Deppert, 1985, J. Virol. 56:541–548). However, heretofore, the role of palmitylation in viral replication and assembly has been poorly understood.

5.1. PALMITYLATION OF INFLUENZA HA AFFECTS VIRUS FORMATION

The carboxy-terminal sequences of the influenza virus HAs of 14 subtypes show remarkable conservation of three cysteine residues which have been shown to be modified by the covalent attachment of palmitic acid. Despite the belief that influenza virus genome sequences are not strongly conserved in the absence of a functional requirement, no significant biological role has been found for palmitylation of these cysteines. In fact, it has been reported that substitution of the conserved cysteines does not affect the rate of intracellular transport or the receptor-binding and fusion activities of the mutant HA proteins and that the cytoplasmic tail cysteine residues appear not to be required for the virus to be infectious (Naim et al., 1992, J. Virol. 66:7585–7588; Simpson & Lamb, 1992, J. Virol. 66:790–803; Steinhauer et al., 1991, Virology 184:445–448; Veit et al., 1991, J. Virol. 65:2491–2500).

Single or multiple mutations of the conserved cysteines were engineered into the cytoplasmic tail of the HA and introduced these changes into the genome of influenza virus transfectants. It was found that several changes of the cysteine positions did not lead to rescued viruses and that other cysteine changes resulted in viruses with attenuated phenotypes. These findings support the notion that the conserved cysteines play a biological role in maintaining the structure of the cytoplasmic tail and/or in offering palmitate attachment at these sites.

In the working examples, described infra, mutations were introduced into the cytoplasmic tail of HA of influenza A/WSN/33 virus (H1 subtype) at positions 553, 560 and 563 (C553, C560 and C563). These positions were changed to serine, alanine, or tyrosine, and the biological effects of the mutants were analyzed. The results show that palmitylation is significant and that the ability to form infectious viral particles correlates with maintenance of the sites possessing the highest level of palmitylation (C563 possessing the highest level and C553 the lowest).

In particular, mutants which lack a cysteine at position 553 could be rescued and, in fact, mutant C553A grows like wild-type. It is thus unlikely that palmitylation at this site would be of crucial importance for virus formation. In addition, Naim et al., supra, have shown that C553 incorporated only about 10% of the total $^3$H-palmitate covalently attached to the HA. Although Naim et al., supra, used an H2 subtype HA (A/Japan/305/57) for the quantification of the palmitylation levels, similar modification levels are assumed for the A/WSN/33 virus HA (H1), since this virus' 17 carboxy-terminal amino acids are identical to those of the A/Japan/305/57 virus. However, recent results demonstrate that in deletion mutants where the cytoplasmic domain of HA, including the cysteines at positions 563 and 560 have been eliminated, the truncated HA is completely palmitylated at position 553, and virus can be rescued.

The cysteine residue at position 560 was shown to contain about 40% of the incorporated palmitate (Naim et al., 1992, supra). When this position was replaced by alanine, the mutant (C560A) was found to be highly attenuated. This finding is compatible with the idea that palmitylation at position 560 is not absolutely required for formation of infectious virus but that it has an accessory role. Finally, viruses with mutations at position 563 of the HA could not be rescued. This cysteine is conserved in the HAs of all 14 subtypes and, according to Naim et al. 1992, supra, it has the highest palmitylation level. Also, all mutant viruses with changes in two or three of the palmitylation sites were not viable.

The fact that substitutions of cysteines by different amino acids had different effects on the phenotype of viruses also indicates a role for the structure in this region. Mutations to serine are more disruptive to viral growth than those to alanine: mutant C553S shows a delay in particle formation and grows to about a 5 fold lower titer than wild-type, whereas mutant C553A grows normally (FIG. 4A). Furthermore, mutant C560S was not viable but C560A was rescued. Following expression using an SV40 vector, a mutant HA protein with a serine at this position incorporated only about 50% of the fatty acid compared to mutant proteins containing either tryptophan or tyrosine (Naim et al., 1992, supra). Thus, a serine at position 560 can affect the efficiency of palmitylation at other positions, presumably by changing the peptide structure in the HA tail. This indirect effect of serine at position 560 on the palmitylation at position 563 might be the reason that the mutant C560S was not rescued.

Surprisingly, mutant C560F was only marginally attenuated. Since a phenylalanine is present at position 560 in the subtype H13 HA, this amino acid might provide the optimal alternative structure to cysteine. This interpretation is supported by the finding of Sugrue and colleagues, who showed that the conserved and palmitylated cysteine in M2 (position 50) is changed to a phenylalanine in some equine influenza virus strains (Sugrue et al., 1990, Virology 179:51–56). Since phenylalanine is a large hydrophobic amino acid it might functionally replace a modified cysteine.

The mutant C560Y grows to peak titers about 2 logs less than wild-type. Several independent revertants have been characterized and the tyrosine was always changed back to cysteine by a single A to G nucleotide change. Single nucleotide changes of the tyrosine codon can encode other amino acids, such as histidine (transition), or asparagine, aspartic acid, phenylalanine and serine (transversion). However, none of these amino acids were observed in these revertants. This suggests that a cysteine is indeed the preferred amino acid at position 560. However, since only 4 revertants were sequenced and since every possible amino acid replacement at position 560 was not tested, the possibility that other amino acids are also well tolerated cannot be excluded. An explanation for the growth advantage of the wild-type virus is that a palmitylated cysteine in this position favors virus assembly.

The data described herein indicates a biological significance for the conserved cysteines in the cytoplasmic tail of the HA of influenza viruses, and thus add a new dimension to the data obtained by others (Naim et al., 1992, supra; Simpson & Lamb, 1992, supra). In those earlier studies, HA mutants (subtype H2 and H3) with substituted cysteine residues were shown to complement the temperature-sensitive, transport-defective influenza virus mutant ts61S. The transiently expressed mutant HA proteins were incorporated into infectious viral particles. However, this type of complementation experiment cannot address the question of whether the cytoplasmic sequences of the HA are required for virus budding or other biologically important steps, because at nonpermissive temperature palmitylated fragments of the ts61S HA may have been synthesized and they would have been capable of initiating virion assembly, as recently discussed by Naim & Roth (Naim & Roth, 1993, J. Virol. 67:4831–4841). On the other hand, the possibility that the cysteines in the H2 or H3 subtype HAs used for the earlier studies play a less crucial role than in the influenza A/WSN/33 HA, which belongs to the H1 subtype, cannot be ruled out. In summary, the data described herein demonstrate that a biological function for the conserved carboxy-terminal cysteines in an H1 HA subtype appear to be required for the formation of infectious virus particles. A change of one or more of the cysteine residues can alter the overall level of palmitylation of the HA and thus affect the assembly process. Alternatively, the palmitylation of a distinct cysteine (C563) in the HA may be crucial for infectivity.

5.2. ASSAYS FOR COMPOUNDS THAT INHIBIT PALMITYLATION OF INFLUENZA HA

The assays described herein are designed to measure palmitylation of appropriate substrates including but not limited to the HA viral protein, HA expression products synthesized by genetically engineered cells, and synthetic peptides corresponding to the cytoplasmic domain of HA, and functional equivalents thereof (herein after referred to as "HA-substrate"). These assays are conducted in cells or in vitro, and can be used to identify substances that inhibit palmitylation of HA, and the production of infectious virus. In the assays of the invention, an HA-substrate, e.g., a protein or peptide having the sequence motif of the HA cytoplasmic domain, is reacted in cells or in vitro with palmitate or a donor of the palmitate residue, in the presence of the protein acyltransferase enzyme responsible for palmitylation, (hereinafter referred to as palmitate transferase, or "PT"). Incorporation of the palmitate residue into the HA-substrate is an indication of palmitylation and PT activity. Inhibition of the incorporation of the palmitate residue by a test substance indicates the ability of the test substance to block palmitylation of HA products and inhibit the formation of infectious virus.

In the assays of the invention, incorporation of the palmitate group into the HA-substrate may be detected by a variety of methods. For example, palmitylation of the HA-substrate can be detected by a change in the mobility of the reaction product as determined by chromatographic methods, including but not limited to TLC (thin layer chromatography), HPLC (high performance liquid chromatography); or electrophoretic methods such as SDS-PAGE. Additionally, either substrate, the HA-substrate or the palmitate, may be labeled so that detection of the label in the reaction product can be used as an indicator of palmitylation and enzyme activity. To this end, a variety of signal generating compounds, including but not limited to radiolabels, fluorogenic compounds, calorimetric compounds, enzymes, etc. may be incorporated into either substrate using standard metabolic labeling techniques or chemical conjugating techniques known in the art. Antibodies specific for either substrate may be used to isolate and/or capture the reaction product. Where solid supports are utilized, one of the reactants can be immobilized on the surface of the support by non-covalent or covalent attachments. For example, the immobilization of proteins such as anti-HA or an HA-substrate can be accomplished by coating the support with a solution of the protein and drying. The coated supports may be prepared in advance and stored prior to use.

The screening assays and the components described below are designed to identify compounds that inhibit the palmitylation of influenza HA. However, the same approach and design can be used to identify inhibitors of palmitylation of any other viral protein crucial for viral infectivity, replication, and/or assembly.

5.2.1. ASSAY COMPONENTS

The HA-substrate, the palmitate donor or the palmitate precursor and the PT enzyme which form the components of the reaction, may be obtained in a variety of ways.

The cell screening assays utilize virus-infected cells, or genetically engineered cells that express HA-substrates in cells which are capable of palmitylation. Such cells or cell lines may be engineered to express HA or peptides corresponding to the cytoplasmic domain of HA using techniques known to those skilled in the art (e.g., see Sambrook et al., 1989, Molecular Cloning: A Laboratory Manual, Cold Spring Harbor Laboratory Press, Cold Spring Harbor, N.Y., which is incorporated by reference herein in its entirety). Such cells provide all the components necessary for the palmitylation reaction and can be used as described herein with labeled palmitate, which is commercially available (e.g., Amersham, New England Nuclear) and/or with antibodies specific for HA or palmitate, that can be used to recover the reaction product from the cells and/or for detection.

Antibodies specific for HA may be prepared by any of a variety of well known techniques. In a preferred embodiment, the antibodies used in the assays should be directed to epitopes of HA that are outside the cytoplasmic domain and/or do not interfere with the palmitylation sites.

For the production of antibodies, various host animals may be immunized by injection with the HA protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72, Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to HA.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

For in vitro assays, the HA-substrate may comprise any protein or peptide that has the required motif for palmitylation. Such HA-substrates include, but are not limited to, unprocessed HA proteins (as used herein, "unprocessed HA proteins" refer to HA proteins which have not been post-translationally modified by the addition of a palmitate residue; i.e., unpalmitylated HA proteins), and peptides corresponding to the cytoplasmic domain of HA.

Unprocessed HA may advantageously be obtained by cloning and expressing the HA gene, or mutants thereof, in any of a variety of prokaryotic expression systems, using recombinant DNA techniques well known in the art (e.g. see Sambrook, 1989, supra.). The HA protein expressed in such prokaryotic systems will not be processed or post-translationally modified as they would be in eukaryotic systems. Alternatively, eukaryotic cell lines that are not capable of palmitylation may be used as expression hosts (e.g. HeLa cells).

Alternatively, the HA-substrates may be chemically synthesized using techniques well known in the art (e.g., see Creighton, 1983, Proteins: Structures and Molecular Principles, W. H. Freeman & Co., NY, Chap. 1).

Whether produced by molecular cloning methods or by chemical synthetic methods, the amino acid sequence of the HA-substrate which may be used in either the cell-based or in vitro assay of the invention need not be identical to the reported sequence of HA (or its cytoplasmic domain). The HA substrates may comprise altered sequences in which amino acid residues are deleted, added, or substituted resulting in a functionally equivalent product that serves as a substrate for palmitylation.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; the negatively charged (acidic) amino acids include aspartic and glutamic acid.

The PT enzyme used in the in vitro assay may be obtained from a variety of sources. For example, PT may be isolated from any of a variety of mammalian cells, tissues or organs using purification schemes described (e.g. see Schmidt and Burns, 1989, Biochem. Soc. Trans. 17:635–626; and Kasinathan et al., 1990, J. Biol. Chem. 265:5139–5144; each of which is incorporated by reference herein in its entirety).

The active enzyme has a molecular weight of 234 kD, and is composed of 65 and 67 kD polypeptides. The enzyme is tightly associated with the membrane of the rough endoplasmic reticulum; therefore, membrane lipids may have to be included in the reaction mixture. Alternatively, crude lysates of cells which express PT, or cytosolic fractions (e.g., cellular microsomal fractions) of cells, tissues or organs that express PT may be utilized as a component of the assay systems.

Once PT is purified to homogeneity, specific antibodies may be generated and the amino acid sequence of PT can be determined, in whole or in part, using standard sequencing techniques, e.g., Edman degradation (see, e.g., Creighton, 1983, supra at pp. 34–49). These amino acid sequences (whole or partial) may then be used to derive and synthesize nucleotide coding sequences for PT which can be used to clone the PT gene and/or cDNA using techniques known in the art, and to express the PT gene product using appropriate expression/host cell systems known in the art. For example, cDNA and/or genomic libraries can be screened with oligonucleotide probes for PT; expression libraries can be screened with antibody, (see, e.g., Sambrook et al., 1989, supra). Alternatively, oligonucleotides derived from PT amino acid sequences could be used as primers in PCR (polymerase chain reaction) to generate cDNA or genomic copies of PT sequences from a variety of cellular sources. For a review of such PCR techniques, see for example, Gelfand, DH, 1989, PCR Technology: Principles and Applications for DNA Amplification, ed., H. A. Ehrlich, Stockton Press, NY, and Current Protocols in Molecular Biology, Vol. 2, Ch. 15, eds., Ausubel et al. John Wiley & Sons, NY, 1988). The PT coding sequence can then be engineered into appropriate expression systems to produce ample quantities of enzyme; e.g., such expression systems may include the use of integrating or non-integrating expression vectors, appropriate promoter/enhancer elements, selectable/amplifiable markers, and the like. (See Sambrook et al., 1989, supra).

Alternatively, the PT protein could be produced using chemical methods to synthesize the amino acid sequence in whole or in part (e.g., see Creighton, 1983, supra, pp. 34–49 and 50–60).

Palmitate may be obtained from a variety of commercial sources, (e.g., Sigma) and may be labeled with any of a variety of signal-generating compounds, including but not limited to radiolabels, fluorogenic compounds, calorimetric compounds enzymes, etc. using standard metabolic labeling techniques or chemical conjugating techniques. Indeed, radiolabeled palmitate is commercially available (e.g. Amersham; New England Nuclear).

Labeled precursors of palmitic acid may include $^{14}C$ or $^{3}H$, and are commercially available (e.g. Amersham; New England Nuclear).

5.2.2. CELL SCREENING ASSAY

This assay detects compounds that inhibit palmitylation of influenza HA in influenza-infected cells, or in cells engineered to express an HA-substrate. The general operation involves adding labeled palmitic acid or a labeled precursor of palmitic acid, with and without the test compound, to the cells, recovering HA or the HA-substrate from the cells, and detecting whether the labeled palmitic acid or a labeled precursor of palmitic acid was incorporated into the HA or HA-substrate recovered. The use of labeled precursors of palmitic acid allows for detection of compounds that may interfere with the biosynthesis of palmitate such that a selective inhibition of infectious virus formation is achieved. The use of labeled palmitic acid or labeled precursors of palmitic acid allows for detection of compounds that may interfere with the attachment of palmitate to the viral HA, such that a selective inhibition of infectious virus formation is achieved. Either the labeled precursor of palmitic acid or the labeled palmitic acid may be used to detect compounds that remove palmitate from HA, and inhibit the formation of infectious influenza virus.

In one embodiment, the test compound and the labeled palmitic acid or labeled precursor of palmitic acid are added to a culture of cells infected with influenza. In an alternate embodiment, the test compound and labeled palmitic acid or labeled precursor of palmitic acid are added to a culture of cells specifically engineered to express the influenza virus HA gene product or other HA-substrate. The use of infected cells in the assay system offers an advantage, in that inhibition of viral infection, replication, and/or assembly can also be assayed. Infected cell assays may also identify viral inhibitors that work on targets other than the palmitylation of HA. The use of genetically engineered cells that express the HA gene product or HA-substrate will identify only those components that specifically inhibit palmitylation of HA.

The order of addition of the test compound and the palmitic acid or labeled precursor of palmitic acid may be varied; e.g., simultaneous or sequential additions may be performed and can provide different information. For example, the prior addition of the test compound will identify compounds that prevent palmitylation of HA. The addition of the test compound subsequent to the addition of labeled palmitate could be used to identify compounds that remove palmitate from HA. No test compound, or a placebo, is added to the controls.

After a suitable time period, viral HA or the genetically engineered HA gene product or HA-substrate is isolated from the culture. This may be accomplished by lysing the cells and isolating HA from the lysates with an anti-HA antibody; e.g., an immobilized anti-HA antibody that will capture and anchor. This system allows for rapid high throughput screening or test compounds. Alternatively, the HA can be isolated from the lysate by immunoprecipitation of immunoelectrophoresis (e.g., Western blot).

The presence or absence of labeled palmitic acid incorporated into the isolated HA is then detected. If the test compound can prevent the palmitylation of influenza HA, the HA-protein or substrate will not incorporate the labeled palmitic acid and the assay will be scored by the absence of the incorporation of label. If a test compound does not inhibit HA palmitylation, the protein will incorporate the label and the labeled protein will be detected by the techniques described above.

5.2.3. IN VITRO SCREENING ASSAY

This assay detects compounds that inhibit the palmitylation of influenza HA in vitro. The principle of the assay involves adding the test compound and labeled palmitic acid to a reaction mixture containing HA-substrate, (e.g., an unprocessed HA-protein or peptide) and PT. After a suitable time period, the presence or absence of labeled palmitic acid incorporated into the HA-substrate is detected. The HA-substrate may be removed from the reaction mixture and/or immobilized using anti-HA antibodies as described in the cell based assay systems.

The reaction conditions used may be adjusted to optimize palmitylation activity in vitro. For example, membrane lipids may be added to the system to enhance enzyme activity; appropriate concentrations of cations may be added to the reaction buffer; the pH and temperature should be adjusted to achieve optimal enzyme activity. Likewise, agents such as DTT (dithiothreitol) which protect sulfhydryl groups, may be added to the reaction mixture.

As explained in the cell based assay systems, the order of addition of the test compound relative to the reactants may be varied to distinguish compounds that act by inhibiting or preventing palmitylation, and those that disrupt or remove palmitate from HA.

In one embodiment, the unprocessed HA-substrate is incubated with a test compound, labeled palmitic acid, and a cellular extract or PT. After a suitable reaction time period, the HA-substrate is removed from the reaction mixture; e.g. using anti-HA antibody. In this regard, an immobilized antibody offers a rapid, high throughput approach. For example, the reaction mixture may be added to a microtiter well plate coated with immobilized anti-HA antibody. After unreacted components are removed, e.g. by washing, the captured HA-substrate is assayed for incorporation of labeled palmitate. The ability of the HA-substrate to incorporate the labeled palmitic acid in the presence of the test compound is scored by the retention of the labeled palmitate by the HA protein. If the test compound can prevent the palmitylation of influenza HA, the HA-substrate will not incorporate the labeled palmitic acid and the assay will be scored by the absence of the incorporation of label. If a test compound does not inhibit HA palmitylation, the HA-substrate will incorporate the label. The evaluation of the test compound is by reference to a control experiment in which the test compound is not added, or a placebo is used.

In another embodiment, the HA-substrate may be immobilized prior to the addition of labeled palmitic acid and a cellular extract or PT, and the test compound (membrane lipids may have to be added). To this end, a solution of the HA-substrate can be used to coat a solid support. Alternatively, an anti-HA antibody may be used to coat the support in order to anchor the HA-substrate. The ability of the immobilized HA to incorporate the labeled palmitic acid in the presence of the test compound is scored by the retention of the label by the protein. If the test compound can prevent the palmitylation of influenza HA, the HA-substrate will not incorporate the labeled palmitic acid and the assay will be scored by the absence of the incorporation of label. If a test compound does not inhibit HA palmitylation, the HA-substrate will incorporate the label. The presence or absence of a labeled HA-substrate will be detected by autoradiographic analysis of the immobilized components. The evaluation of the test compound is by reference to a control experiment in which the test compound is not added.

In yet another embodiment of the invention, the palmitic acid is immobilized on a solid support and incubated with HA and a cellular extract or palmitate transferase, and the test compound. The ability of the HA to bind to the immobilized palmitic acid in the presence of the test compound can be scored by using a one-labeled HA protein or a labeled anti-HA antibody. Detection systems for this use can utilize radioactivity, biotin-streptavidin, or fluorescence. If the test compound can prevent the palmitylation of influenza HA, the protein will not bind to the palmitic acid and the assay will be scored by the absence of a bound protein to the palmitic acid. If a test compound does not inhibit HA palmitylation, the protein will bind to the palmitic acid and be detected by the techniques so described. The evaluation of the test compound is by reference to a control experiment in which the test compound is not added.

5.3. ASSAYS FOR ANTIVIRAL ACTIVITY

5.3.1. VIRAL GROWTH ASSAYS

The ability of a palmitylation inhibitor to prevent viral growth can be assayed by plaque formation or by other indices of viral growth, such as the $TCID_{50}$ or growth in the allantois of the chick embryo. In these assays, an appropriate cell line is infected with wild-type influenza virus, and the test compound is added to the tissue culture medium either at or after the time of infection. The effect of the test compound is scored by quantitation of viral particle formation as indicated by the presence of viral plaques or by an index such as the $TCID_{50}$, growth in the allantois of the chick embryo, or with a hemagglutination assay.

A palmitylation inhibitor can be scored by the ability of a test compound to depress plaque formation or to reduce the cytopathic effect in virus-infected cells or the allantois of the chick embryo, or by its ability to reduce viral particle formation as measured in a hemagglutination assay.

5.3.2. ANIMAL MODEL ASSAYS

The ability of a palmitylation inhibitor to prevent the replication of influenza virus can be assayed in animal models that are natural or adapted hosts for influenza. Such animals may include mammals such as pigs, ferrets, mice, monkeys, horses, and primates, or birds. As described in detail in Section 5.5 below, such animal models can be used to determine the $LD_{50}$ and the $ED_{50}$ in animal subjects, and such data used to derive the therapeutic index for the palmitylation inhibitor.

5.3.3. HA TITER ASSAYS

The ability of a palmitylation inhibitor to prevent viral growth can be assayed by measuring the HA titer in the supernatants of infected cells or in the allantoic fluids of infected embryonated eggs at various times post-infection.

5.4. INHIBITORY COMPOUNDS

Inhibitory compounds identified in the foregoing screening assays which may be used in accordance with the invention, may include but are not limited to small organic molecules, peptides, and antibodies.

The assays can be used to identify compounds that compete with the cytoplasmic domain of HA as the recipient of palmitate; compounds that block the sites for palmitate attachment on the cytoplasmic domain of HA; and compounds that inhibit activity of the host cell PT enzyme.

Analysis of a number of palmitylated host cell proteins has failed to reveal a consensus palmitylation site (for a review see Deschenes et al., 1990, Current Opinion in Cell Biology 2: 1108–1113). Therefore, compounds which either block the HA palmitylation sites or compete with HA as a substrate may demonstrate higher specificity for inhibiting palmitylation of HA as opposed to host cell proteins. As a result, such compounds may display fewer side effects.

For example, peptides having an amino acid sequence corresponding to the cytoplasmic domain of influenza HA may be used to compete with viral HA as the substrate for palmitylation, and therefore, may be useful as inhibitors in accordance with the invention. Such peptides may be synthesized chemically (e.g. see Creighton, 1983, Proteins-:Structures and Molecular Principles, W. H. Freeman & Co., N.Y., Ch.1) or generated via recombinant DNA techniques (e.g., Sambrook, 1989, Molecular Cloning: A Laboratory Manual, Cold Spring Harbor Laboratories Press, Cold Spring Harbor, N.Y.). Peptides having the following amino acid sequence may be used:

```
NH2-Xn-G S L Q C R I C I-COOH      (SEQ ID NO: 18)
        N I R F N F
          M   Q Y
          C   T
          Y   M
```

Wherein n is an integer from (0–40) and represents one or more amino acids of the transmembrane region of HA located upstream of the depicted sequence; and the amino acids indicated below a residue within the peptide sequence shown may be substituted for that residue.

It should be noted that the decapeptide (NGSLQCRICI) SEQ ID NO: 19 was shown to have insignificant antiviral activity on influenza infection in cell culture, reducing titers by 1–2 logs (see Collier et al., 1991, Virology 183; 769–772; FIG. 1). However, the decapeptide was highly insoluble, requiring the use of a detergent as a carrier, which did not ensure that sufficient amounts of the peptide were delivered into the infected cells. An improved carrier such as lipofectin or liposomes for intracellular delivery may be used to increase the potency of this peptide. Moreover, longer peptides, which include part or all of the HA transmembrane region may work as superior competitors for palmitylation in the infected cell; such peptides may localize within the cellular membrane so that they are more accessible to the cellular PT enzyme. Lipofectin or liposomes which incorporate such peptide in their bilayer may be used to deliver the peptides to cells.

Alternatively, antibodies specific for the cytoplasmic domain of HA and which inhibit the covalent attachment of palmitic acid may be used. Such antibodies may be generated using standard techniques described in Section 5.2.1, supra, against HA, the cytoplasmic domain of HA, or against synthetic peptides. Such antibodies include but are not limited to polyclonal, monoclonal, Fab fragments, single chain antibodies, chimeric antibodies, etc. Where whole antibodies are used, internalizing antibodies are preferred. However, lipofectin may be used to deliver the antibody or a fragment of the Fab region which binds to the HA epitope into cells. Where fragments of the antibody are used, the smallest inhibitory fragment which binds to the cytoplasmic domain of HA is preferred.

In another embodiment, any compound that inhibits the enzyme activity of the cellular PT enzyme responsible for the transfer and covalent attachment of palmitic acid to HA may be used, provided the compound demonstrates low toxicity and a good therapeutic index.

5.5. TREATMENT OF INFLUENZA VIRUS INFECTION USING COMPOUNDS THAT INHIBIT PALMITYLATION OF HA

The particular compound that inhibits palmitylation and viral replication can be administered to a patient at therapeutically effective doses. A therapeutically effective dose refers to that amount of the compound sufficient to result in amelioration of symptoms of viral infection.

Toxicity and therapeutic efficacy of such compounds can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design the delivery system that targets such compounds to the site of infection in order to minimize damage to uninfected cells and reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the therapeutic compounds and their physiologically acceptable salts and solvates may be formulated for administration by inhalation or insufflation (either through the mouth or the nose) or for oral, buccal, parenteral or rectal administration.

For administration by inhalation, the compounds for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

The therapeutic compounds may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The therapeutic compounds may also be formulated in rectal compositions such as suppositories or retention enemas, e.g containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

6. EXAMPLE: MUTATIONS AT PALMITYLATION SITES OF INFLUENZA HA PROTEIN AFFECT VIRUS FORMATION

In the example described below, mutations were introduced into the HA of influenza A/WSN/33 virus (H1 subtype) by reverse genetics techniques (see U.S. Pat. No. 5,166,057, which is incorporated by reference herein in its entirety). It was found that the cysteine at position 563 of the cytoplasmic tail is required for infectious particle formation. The cysteine at position 560 can be changed to alanine or tyrosine to yield attenuated strains, while a change from cysteine in position 553 to serine or alanine does not significantly alter the phenotype of the virus. None of the double or triple mutations resulted in infectious virus. Selection of revertants of the attenuated cysteine to tyrosine mutant (position 560) always resulted in reversion to cysteine rather than to other amino acids.

6.1. MATERIALS AND METHODS

6.1.1. VIRUS AND CELLS

Influenza A HK-WSN (H3N1) virus was used as helper virus as described previously (Enani and Palese, 1991, J. Virol. 65:2711–2713; U.S. Pat. No. 5,166,057). HK-WSN virus is a reassortant virus which contains seven genes from A/WSN/33 (H1N1) virus and the HA gene from A/Hong Kong/8/68 (H3N2) virus. HK-WSN virus was propagated in Madin-Darby bovine kidney (MDBK) cells and titrated by plaguing on MDBK cells. MDBK cells were used for RNP transfection and for the selection of the transfectant viruses as well as for preparation of virus stocks (Luytjes et al., 1989, Cell 59:1107–1113). Multiple passaging of viruses in MDBK cells or in embryonated eggs was done by using inocula derived from the sample of the previous passage having the highest titer. Dilutions between $\frac{1}{10}$ and $\frac{1}{1000}$ were used for inoculation.

6.1.2. GROWTH CURVES IN MDBK CELLS

Confluent monolayers of MDBK cells in 60 mm dishes were infected with virus at a multiplicity of infection (moi) of 0.001 for one hour at room temperature and incubated at 37° C./5% $CO_2$ after addition of culture medium. The virus titer at 12-hr intervals post infection was determined by plaque assay or $TCID_{50}$ assay. The latter assay was used for titrating mutant viruses which did not form discrete plaques.

6.1.3. OLIGONUCLEOTIDE-DIRECTED MUTAGENESIS OF THE PALMITATE ADDITION SITES OF HA

Plasmid pT3/WSN-HA containing the full length cDNA of the wild-type HA gene of influenza A/WSN/33 virus (Enami and Palese, 1991, J. Virol. 65:2711–2713) was used for the construction of all the mutant constructs. In order to facilitate the introduction of mutations into the 3' end of the cDNA, pT3/WSN-HA was modified in the following way. A HindIII restriction enzyme site was introduced at nucleotide position 1679 (16 amino acids away from the carboxy terminus) and the HindIII site between the T3 promoter and the pUC18 vector of the original pT3/WSN-HA clone was replaced by a PstI site. For this purpose pT3/WSN-HA was first linearized with HindIII and the ends were filled in with Klenow enzyme (Bethesda Research Laboratories). Secondly, the linearized vector was digested with BstXI and purified by gel electrophoresis. A PCR fragment was generated by using pT3/WSN-HA DNA as a template and two synthetic oligonucleotides as primers. The upstream primer (5'-CTGTCGCCAGTTCACTGGTGCTTTTG-GTCTCCCTGGGGGC AAGCTTCTGGATGTGT-3') SEQ ID NO: 20 covers the sequences from nucleotide 1636 to 1695 of the HA cDNA, and contains a BstXI site and a HindIII site (underlined) generated by introducing silent mutations at nucleotide positions 1679 and 1682 (bold). The downstream primer HA01 (5'-CCGGCCTGCAGAATTAACCCTCACAAA-3') SEQ ID NO: 21 contains a T3 promoter and a PstI site (underlined). The PCR fragment was digested with BstXI and ligated into the previously described vector. The modified plasmid was designated pT3/WSN-HA/HindIII.

The mutant plasmids shown in FIG. 2 were constructed by oligonucleotide-directed mutagenesis. To create pC553S, for instance, a DNA fragment was amplified by PCR using pT3/WSN-HA/HindIII as template and the primers HA01 and the oligonucleotide (5'-CCGG TTTCTGGATGTCTTCTAATGGGTC-3') SEQ ID NO: 22 containing the HindIII site (underlined) and the appropriate mutation (bold) in the open reading frame of the HA. The PCR fragment was digested with HindIII and PstI and inserted into pT3/WSN-HA/HindIII digested with HindIII and PstI. All mutant plasmids were constructed in this manner using appropriate primers and templates. The inserts of all the mutant plasmids were confirmed by sequencing (Sanger et al., 1977, Proc. Natl. Acad. Sci. USA 74:5463–5467).

In order to express wild-type and mutant HA proteins the XbaI-PstI fragments of pT3/WSN-HA/HindIII and of the mutant constructs, containing the entire coding and non-coding regions of the HA were subcloned into the expression vector pSVK3 (Pharmacia), downstream of the T7 promoter.

6.1.4. PURIFICATION OF INFLUENZA A VIRUS RNA POLYMERASE COMPLEX AND RIBO-NUCLEOPROTEIN (RNP) TRANSFECTION OF MDBK CELLS

The RNA polymerase complex was purified from influenza A/PR/8/34 virus or X-31 as described (Parvin et al., 1989, J. Virol. 63:5142–5152) and was then used for RNP transfection of MDBK cells. The transfection procedure followed the protocol provided earlier (Enami and Palese, 1991, J. Virol. 65:2711–2713; U.S. Pat. No. 5,166,057) except that the transfection yield was passaged twice in liquid on MDBK cells in the presence of 0.5% rabbit anti-HK antiserum (Wigler et al., 1979, Proc. Natl. Acad. Sci. USA 77:3567–3570). Viruses were plaque-purified in the presence of 0.5% rabbit anti-HK antiserum.

6.1.5. VIRUS PURIFICATION AND RNA EXTRACTION

The wild-type and mutant transfectant viruses were propagated in MDBK cells and then purified by 30% to 60% sucrose gradient centrifugation. Virion RNA was then extracted as described previously (Luo et al., 1992, J. Virol. 66:4679–4685).

6.1.6. RNA AND DNA SEQUENCING

The sequence of the HA gene of the transfectant viruses C553S, C553A and C560A were verified by direct RNA sequencing using the primer 5'-GGTGTATCAGATTCTGGCGATC-3' SEQ ID NO: 23 (corresponding to position 1607–1628 of the A/WSN HA gene) and AMV reverse transcriptase. The sequence of the HA segments of all the other mutant viruses was obtained as follows: RNA from purified virus was transcribed into a cDNA using AMV reverse transcriptase and the primer 5'-ACGTGGATCCGAAAGTGTAAGAAATGGG-3' SEQ ID NO: 24 which is complementary to positions 1509–1526 of the A/WSN HA virion RNA and contains a BamHI site (underlined). This oligonucleotide and the primer 5'13/HindIII (ATGCTCTAGAAGCTTAGTAGAAACAAGG) SEQ ID NO: 25 were used for subsequent PCR amplification of the cDNA. The sequence of oligonucleotide 5'13/HindIII corresponds to the 13 conserved nucleotides at the 5' end of the virion RNA and Contains a HindIII site. HindIII fragments of the PCR products were subcloned into pUC19 and sequenced by standard methods (Sambrook et al., 1989, Molecular Cloning: A Laboratory Manual. Cold Spring Harbor Laboratory Press. Cold Spring Harbor, NY; Sanger et al., 1977, Proc. Natl. Acad. Sci. USA 74:5463–5467).

6.1.7. EXPRESSION OF HA IN TRANSFECTED COS-7 CELLS

For transient expression of HA cDNA cloned into pSVK3, subconfluent monolayers of COS-7 cells were infected with a recombinant vaccinia virus expressing the T7 RNA polymerase (vTF7.3) (Feurst et al., 1986, Proc. Natl. Acad. Sci. USA 83:8122–8125) for 1 hour at an moi of 5. Ten mg of plasmid DNA were transfected into a 60 mm dish by the calcium phosphate precipitation method (Wigler et al., 1979, Proc. Natl. Acad. Sci. USA 77:3567–3570). 16 hours post transfection the cells were fixed with 3% paraformaldehyde and surface expression was determined by indirect immunofluorescence (Staehell et al., 1986, Cell 65:147–158). The H1 HA specific monoclonal antibody 2G9 (Li et al., 1993, J. Virol. 67:6659–6666) was used as the first antibody and a rhodamine-coupled goat anti-mouse antibody (Boehringer-Mannheim) for the second antibody.

6.2. RESULTS

6.2.1. DESIGN AND CONSTRUCTION OF CARBOXY TERMINAL MUTANTS OF INFLUENZA VIRUS A/WSN/33 VIRUS HA

Oligonucleotide-directed mutagenesis was performed on a cDNA copy of the A/WSN/33 HA to introduce mutations into the region encoding the carboxy terminus. The cysteine residues at positions C553, C560 and C563 have been associated with palmitylation of the HA in other HA subtypes (Naeve and Williams, 1990, EMBO J. 9:3857–3866; Naim et al., 1992, J. Virol. 66:7585–7588; Steinhauer et al., 1991, Virology 184:445–448; Veit et al., 1991, J. Virol. 65:2491–2500). These positions were first changed to serine or alanine and the biological effects of these mutants were analyzed (FIG. 2). Mutant S558C/C560S was constructed since the HA of subtype H13 contains a cysteine in position 558 but not in position 560 (FIG. 1). This mutant now possesses a potential palmitylation site in position 558 instead of 560. In addition, position C560 was changed to phenylalanine or tyrosine. The C560 to phenylalanine change was done because this sequence is present in the H13 subtype of the HA (FIG. 1). The single substitution of C560 with a tyrosine was previously shown to result in a protein with a phenotype quite different from that of the wild-type protein (Brewer et al., 1991, J. Cell Biol. 114:413–421; Lazarovits & Roth, 1988, Cell 53:743–752). Whereas the wild-type HA was excluded from coated pits, the mutant HA protein was efficiently internalized and was in addition transported to the basolateral rather than the apical membrane.

6.2.2. RESCUE OF MUTANT VIRUSES

The experiments described herein were designed to test whether viruses with these mutant HA proteins could form infectious virus particles. In order to rescue the mutated HA genes ribonucleoprotein (RNP) transfections were performed using HKWSN (H3N1) as a helper virus (Enami and Palese, 1991, J. Virol. 65:2711–2713). As shown in FIG. 2, viruses were isolated after transfection of RNAs encoding single changes of C553 to serine or to alanine, suggesting that this cysteine position in the HA is not crucial for the formation of viable virus. The cysteine at position 560 could be changed to alanine, tyrosine or phenylalanine and viable viruses could still be rescued. However, a change to serine at this position (C560S) did not result in a viable transfectant virus. In order to rule out the possibility that an unaccounted mutation in the main portion of the HA abrogated the rescue of mutant C560S virus, the region encoding the cytoplasmic portion of pC560S was replaced with the corresponding one of the wild-type. Transfection of this plasmid (pC560S/wt) resulted in the rescue of a transfectant influenza virus. Mutants with changes in position C563 to alanine or serine were also not rescued. Replacement of the region encoding the cytoplasmic portion of pC563S with the corresponding wild-type sequence again resulted in rescue of a transfectant virus, suggesting that the cysteine in position 563 is critical. Furthermore, mutants in which two or three of the conserved cysteine residues were substituted by alanine or by serine were not rescued. Mutant S558C/C560S was also not rescued, suggesting a structural incompatibility of serine at position 560. Alternatively, the introduced cysteine at position 558 may not be able to serve as a palmitate addition site.

In all instances when a mutant virus was not rescued, RNP transfections were repeated two or more times under well controlled conditions. In these experiments, rescue of approximately 103 wild-type transfectants per ml virus supernatant was routinely achieved. Furthermore, the most attenuated mutant (C560A) was consistently rescued (see below). In addition, all mutant plasmids were shown to yield RNA levels in vitro similar to that obtained using pT3WSN-HA/HindIII (wild-type). These results indicate that mutations which do not result in the rescue of virus under the experimental conditions used herein abrogate or seriously impair the function of the HA.

6.2.3. EXPRESSION OF MUTATED HA IN TRANSFECTED CELLS

In order to confirm that the mutant constructs encode HA proteins which are expressed on the cell surface, the HA cDNAs were subcloned into the expression vector pSVK3 and tested for cell surface expression by indirect immunofluorescence. All the mutant HA genes that were not rescued into live viruses encoded proteins whose expression at the cell surface was indistinguishable from that of the wild-type HA. Immunofluorescence of the wild-type HA and of the mutants C560S, C563A, C560A/C563A and C553S/C56OS/C563S are shown in FIG. 3. The introduced mutations did not significantly affect the biosynthesis and the transport of the mutant HA proteins, confirming previously published results (Naeve & Williams, 1990, EMBO J. 9:3857–3866; Naim et al., 1992, J. Virol. 66:7585–7588; Simpson & Lamb, 1992, J. Virol. 66:790–803; Steinhauer et al., 1991, Virology 184:445–448; Veit et al., 1991, J. Virol. 65:2491–2500).

6.2.4. GROWTH PROPERTIES OF TRANSFECTANT VIRUSES

The growth features of the transfectants were characterized in MDBK cells (FIG. 4). The mutation of the conserved cysteine in the membrane anchoring region barely affected viral growth. Mutant C553A behaves like the wild-type control, whereas the mutant virus C553S showed a reproducible delay in virus release and grew only to a 5-fold lower titer than wild-type virus (FIG. 4A). However, mutant C560A grew to 50-fold lower titers than the wild-type virus (FIG. 4A). Interesting results were obtained when position C-560 was changed to different amino acids. Whereas mutant C560Y was as attenuated as C560A virus, mutant C560F reached—with delays—final titers comparable to those of wild-type virus (FIG. 4B).

6.2.5. GENERATION OF REVERTANTS BY PASSAGING OF ATTENUATED MUTANTS

The importance of the conserved cysteine in position 560 of the cytoplasmic tail of the HA was studied by attempting to select for revertant viruses of the attenuated mutants C560Y and C560A. Whereas only one nucleotide change is sufficient to change the codon for tyrosine (TAC) to that for cysteine (TGC), two nucleotide changes would be necessary to change an alanine (GCC) to a cysteine (TGC). Both mutants could alter position 560 by single point mutations resulting in a variety of amino acids other than cysteine.

A preparation of mutant virus C560Y was grown by inoculating a 75cm$^2$ tissue culture flask of MDBK cells with virus from a single plaque. The resulting preparation, with a titer of $4 \times 10^6$ TCID$_{50}$/ml, contained about $10^4$ particles which formed plaques of wild-type characteristics. Viruses from two large plaques of two independent virus preparations were further plaque-purified and viral RNA was prepared for sequencing. In all four cases the tyrosine had reverted to a cysteine. Since there is a mutation in the 5' noncoding region (position 1739, T to C change) of the original plasmid construct (pC560Y), these viruses can be identified as true revertants. Furthermore, viruses obtained from individual small diffuse C560Y plaques were passaged in MDBK cells (7 passages) or in eggs (8 passages). Again, reversion to cysteine occurred as confirmed by sequencing.

Similar experiments were performed with the mutant C560A and neither reversion of the attenuated phenotype nor changes in the mutated sequences were observed. This result is most likely due to the fact that a reversion from alanine to cysteine would require the simultaneous change of two nucleotides. Seven passages in MDBK cells of the marginally attenuated mutant C560F did not result in a sequence change in this position (as confirmed by sequence analysis).

7. EFFECT OF CERULENIN ON VIRUS FORMATION

The following example demonstrates that a compound known to inhibit palmitylation, cerulenin, inhibits production of infectious influenza virus in cell culture. However, cerulenin is a toxic compound with many side effects and would not be selected as a drug of choice in accordance with the invention.

7.1. MATERIALS AND METHODS

7.1.1. EFFECT OF CERULENIN ON HA TITER

MDBK cells were infected with wild-type influenza virus at an MOI of 1. At 6 hours post-infection, various concentrations of cerulenin were added to the medium (0–20 ug/ml). The HA titer was assayed at 12 and 24 hours post-infection.

7.1.2. EFFECT OF CERULENIN ON VIRUS FORMATION

MDBK cells were infected with wild-type influenza virus at an MOI of 1. At 1 hour post-infection, various concentrations of cerulenin were added to the medium (0–10 ug/ml). After 20 hours of incubation, the viral titer was assayed (PFU/ml).

7.2. RESULTS

7.2.1. EFFECT OF CERULENIN ON HA TITER

Cerulenin was able to depress HA titer as a function of concentration when HA levels were quantitated at either 12 or 24 hours post-infection relative to levels observed in the absence of the drug (Table I).

TABLE I

Effect of Cerulenin on HA Titer

| Cerulenin* (ug/ml) | HA titer | |
|---|---|---|
| | 12 hr p.i. | 24 hr p.i. |
| 0 | 7 | 7 |
| 2 | 7 | 7 |
| 10 | 3 | 4 |
| 20 | 0 | 0 |

*Cytotoxic effects of cerulenin have been observed at concentrations of 8 µg/ml or greater.

7.2.2. EFFECT OF CERULENIN ON VIRUS FORMATION

Influenza viral titer decreased as a function of cerulenin concentration when virus was recovered after a 20-hour incubation with the drug (Table II). At concentrations exceeding 6 µg/ml, the viral titer was reduced 3–4 logs relative to that observed in the absence of the drug.

TABLE II

Effect of Cerulenin on Virus Formation

| Cerulenin (µg/ml) | Pfu titer (pfu/ml) |
|---|---|
| 0 | $2 \times 10^7$ |
| 2 | $\sim 10^7$ |
| 4 | $\sim 10^7$ |
| 6 | $2 \times 10^7$ |
| 8 | $1 \times 10^4$ |
| 10 | $2 \times 10^3$ |

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An assay for identifying a potential anti-viral compound that inhibits the palmitylation of a cysteine residue of an influenza hemagglutinin and thereby inhibits late stages of viral life cycle and production of infectious virus, comprising:
- (a) providing cells infected with an influenza virus that has a hemagglutinin gene product characterized by a cysteine residue in the penultimate position of the cytoplasmic tail;
- (b) adding palmitate and a test substance to the influenza virus-infected cell;
- (c) detecting whether the palmitate is incorporated into influenza virus hemagglutinin recovered from the infected cell, in which the ability of the test substance to inhibit palmitylation is indicated by a decrease in incorporation of the palmitate into the hemagglutinin as compared to the amount of palmitate incorporated into the hemagglutinin in the absence of the test substance.

2. The assay of claim 1 in which the palmitate is labeled with a signal-generating compound.

3. The assay of claim 2 in which the signal-generating compound is a radiolabel, a fluor, an enzyme or a colorimetric signal-generating compound.

4. The assay of claim 1 in which the influenza virus hemagglutinin substrate is recovered from the cell and immobilized on a solid surface.

5. The assay of claim 4 in which the influenza virus hemagglutinin substrate is captured by an immobilized antibody specific for hemagglutinin.

6. The assay of claim 1 in which the hemagglutinin has the following amino acid sequence at the cytoplasmic domain:

$XGX^1X^2X^3X^4X^5X^6CI$ SEQ ID NO: 18 in which

X when present=N;

$X^1$=S or N;

$X^2$=L, I, M, C or Y;

$X^3$=Q or R;

$X^4$=C or F;

$X^5$=R, Q, T, M, or N; and $X^6$=I, F, or Y in which the amino acid sequence is depicted using the single letter code.

7. The assay of claim 1 or 6 wherein the test substance does not significantly inhibit cellular fatty acid biosynthesis.

8. The assay of claim 1 or 6 wherein the amount of the test substance needed to inhibit hemagglutinin palmitylation is not toxic to the cell.

9. The assay of claim 1 or 6 wherein the test substance shown to decrease the amount of hemagglutinin palmitylation is further assayed by:
- a. contacting influenza virus-infected cells with the test substance; and
- b. determining whether the viral titer is decreased in the presence of the test substance as compared to in its absence.

* * * * *

UNITED STATES PATENT AND TRADEMARK OFFICE
CERTIFICATE OF CORRECTION

| | | |
|---|---|---|
| PATENT NO. | : 6,150,131 | Page 1 of 1 |
| APPLICATION NO. | : 08/737841 | |
| DATED | : November 21, 2000 | |
| INVENTOR(S) | : Palese | |

It is certified that error appears in the above-identified patent and that said Letters Patent is hereby corrected as shown below:

At column 1, line 10 of the patent, please insert the following:

-- STATEMENT REGARDING FEDERALLY SPONSORED RESEARCH OR DEVELOPMENT

This invention was made with government support under grant No. AI018998 awarded by the National Institutes of Health. The government has certain rights in the invention. --

Signed and Sealed this

Twenty-sixth Day of April, 2011

David J. Kappos
*Director of the United States Patent and Trademark Office*

```
                           SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 13 amino acids
         (B) TYPE: amino acid
         (D) TOPOLOGY: unknown (ii) MOLECULE TYPE: peptide (xi) SEQUENCE DESCRIPTION: SEQ ID NO:1:

Met Cys Ser Asn Gly Ser Leu Gln Cys Arg Ile Cys Ile
1               5                   10

(2) INFORMATION FOR SEQ ID NO:2:

(i) SEQUENCE CHARACTERISTICS:
         (A) LENGTH: 13 amino acids
         (B) TYPE: amino acid
         (D) TOPOLOGY: unknown (ii) MOLECULE TYPE: peptide (xi) SEQUENCE DESCRIPTION: SEQ ID NO:2:

Met Cys Ser Asn Gly Ser Leu Gln Cys Arg Ile Cys Ile
1               5                   10

(2) INFORMATION FOR SEQ ID NO:3:

(i) SEQUENCE CHARACTERISTICS:
         (A) LENGTH: 13 amino acids
         (B) TYPE: amino acid
         (D) TOPOLOGY: unknown (ii) MOLECULE TYPE: peptide
```

(xi) SEQUENCE DESCRIPTION: SEQ ID NO:3:

Ala Cys Gln Lys Gly Asn Ile Arg Cys Asn Ile Cys Ile
1               5                   10

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:4:

Ala Cys Gln Asn Gly Asn Ile Arg Cys Gln Ile Cys Ile
1               5                   10

(2) INFORMATION FOR SEQ ID NO:5:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:5:

Met Cys Ser Asn Gly Ser Leu Gln Cys Arg Ile Cys Ile
1               5                   10

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:6:

Met Cys Ser Asn Gly Ser Met Gln Cys Arg Ile Cys Ile
1               5                   10

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:7:

Ile Cys Tyr Lys Asn Gly Asn Met Arg Cys Thr Ile Cys Ile
1               5                   10

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:8:

Gly Met Gln Asn Gly Ser Cys Arg Cys Met Phe Cys Ile

```
1               5                   10
```

(2) INFORMATION FOR SEQ ID NO:9:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:9:

```
Ala Met Ser Asn Gly Ser Cys Arg Cys Asn Ile Cys Ile
1               5                   10
```

(2) INFORMATION FOR SEQ ID NO:10:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:10:

```
Cys Leu Lys Asn Gly Asn Met Arg Cys Thr Ile Cys Ile
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:11:

```
Ala Cys Ser Asn Gly Ser Cys Arg Cys Thr Ile Cys Ile
1               5                   10
```

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:12:

```
Gly Cys Gln Asn Gly Asn Tyr Arg Cys Thr Phe Cys Ile
1               5                   10
```

(2) INFORMATION FOR SEQ ID NO:13:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (xi) SEQUENCE DESCRIPTION: SEQ ID NO:13:

```
Ala Cys Ser Gly Asn Cys Arg Phe Asn Tyr Cys Ile
1               5                   10
```

(2) INFORMATION FOR SEQ ID NO:14:

```
        (i) SEQUENCE CHARACTERISTICS:
            (A) LENGTH: 13 amino acids
            (B) TYPE: amino acid
            (D) TOPOLOGY: unknown (ii) MOLECULE TYPE: peptide (xi) SEQUENCE DESCRIPTION: SEQ ID NO:14:

Met Cys Ser Asn Gly Ser Leu Gln Cys Arg Ile Cys Ile
1               5                   10

(2) INFORMATION FOR SEQ ID NO:15:

(i) SEQUENCE CHARACTERISTICS:
            (A) LENGTH: 36 base pairs
            (B) TYPE: nucleic acid
            (C) STRANDEDNESS: single
            (D) TOPOLOGY: unknown (ii) MOLECULE TYPE: DNA (ix) FEATURE:
            (A) NAME/KEY: CDS
            (B) LOCATION: 1..36

(xi) SEQUENCE DESCRIPTION: SEQ ID NO:15:

TGT TCT AAT GGG TCT TTG CAG TGC AGA ATA TGC TAC                 36
Cys Ser Asn Gly Ser Leu Gln Cys Arg Ile Cys Tyr
1               5                   10

(2) INFORMATION FOR SEQ ID NO:16:

(i) SEQUENCE CHARACTERISTICS:
            (A) LENGTH: 12 amino acids
            (B) TYPE: amino acid
            (D) TOPOLOGY: unknown (ii) MOLECULE TYPE: protein (xi) SEQUENCE DESCRIPTION: SEQ ID NO:16:

Cys Ser Asn Gly Ser Leu Gln Cys Arg Ile Cys Tyr
1               5                   10

(2) INFORMATION FOR SEQ ID NO:17:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /note= "X = Cys, Ser or Ala"

(ix) FEATURE:
            (A) NAME/KEY: Modified-site
            (B) LOCATION: 6
            (D) OTHER INFORMATION: /note= "X = Leu or Cys"

(ix) FEATURE:
            (A) NAME/KEY: Modified-site
            (B) LOCATION: 8
            (D) OTHER INFORMATION: /note= "X = Cys, Ser, Ala, Tyr or
                Phe"

(ix) FEATURE:
            (A) NAME/KEY: Modified-site
            (B) LOCATION: 11
            (D) OTHER INFORMATION: /note= "X = Cys, Ser or Ala"
```

-continued (xi) SEQUENCE DESCRIPTION: SEQ ID NO:17:

```
Xaa Ser Asn Gly Ser Xaa Glu Xaa Arg Ile Xaa Ile
1               5                   10
```

(2) INFORMATION FOR SEQ ID NO:18:

(i) SEQUENCE CHARACTERISTICS:
(A) LENGTH: 10 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 3
(D) OTHER INFORMATION: /note= "X = Ser or Asn"

(ix) FEATURE:
(A) NAME/KEY: Modified-site
(B) LOCATION: 4
(D) OTHER INFORMATION: /note= "X = Leu, Ile, Met, Cys or Tyr"

(ix) FEATURE:
(A) NAME/KEY: Modified-site
(B) LOCATION: 5
(D) OTHER INFORMATION: /note= "X = Gln or Arg"

(ix) FEATURE:
(A) NAME/KEY: Modified-site
(B) LOCATION: 6
(D) OTHER INFORMATION: /note= "X = Cys or Phe"

(ix) FEATURE:
(A) NAME/KEY: Modified-site
(B) LOCATION: 7
(D) OTHER INFORMATION: /note= "X = Arg, Asn, Gln, Thr or Met"

(ix) FEATURE:
(A) NAME/KEY: Modified-site
(B) LOCATION: 8
(D) OTHER INFORMATION: /note= "X = Ile, Phe or Tyr"

(ix) FEATURE:
(A) NAME/KEY: Modified-site
(B) LOCATION: 1
(D) OTHER INFORMATION: /note= "X = X subscript n, wherein n is an integer from (0-40) and represents one or more amino acids of the transmembrane region of HA"

(xi) SEQUENCE DESCRIPTION: SEQ ID NO:18:

```
Xaa Gly Xaa Xaa Xaa Xaa Xaa Xaa Cys Ile
1               5                   10
```

(2) INFORMATION FOR SEQ ID NO:19:

(i) SEQUENCE CHARACTERISTICS:
(A) LENGTH: 10 amino acids
(B) TYPE: amino acid
(D) TOPOLOGY: unknown (ii) MOLECULE TYPE: peptide (xi) SEQUENCE DESCRIPTION: SEQ ID NO:19:

```
Asn Gly Ser Leu Gln Cys Arg Ile Cys Ile
1               5                   10
```

(2) INFORMATION FOR SEQ ID NO:20:

(i) SEQUENCE CHARACTERISTICS:

(A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CTGTCGCCAG TTCACTGGTG CTTTTGGTCT CCCTGGGGGC AAGCTTCTGG ATGTGT          56

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CCGGCCTGCA GAATTAACCC TCACAAA                                          27

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CCGGTTTCTG GATGTCTTCT AATGGGTC                                         28

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GGTGTATCAG ATTCTGGCGA TC                                               22

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

ACGTGGATCC GAAAGTGTAA GAAATGGG                                         28

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued (ii) MOLECULE TYPE: DNA (xi) SEQUENCE DESCRIPTION: SEQ ID NO:25:

ATGCTCTAGA AGCTTAGTAG AAACAAGG                                28